United States Patent [19]

Rosback

[11] 3,943,184

[45] Mar. 9, 1976

[54] AROMATIC HYDROCARBON ISOMER SEPARATION PROCESS

[75] Inventor: Donald H. Rosback, Elmhurst, Ill.

[73] Assignee: Universal Oil Products Company, Des Plaines, Ill.

[22] Filed: Mar. 27, 1975

[21] Appl. No.: 562,604

Related U.S. Application Data

[63] Continuation-in-part of Ser. No. 443,043, Feb. 15, 1974, Pat. No. 3,894,109.

[52] U.S. Cl. .... 260/674 SA; 208/310 Z; 252/455 Z
[51] Int. Cl.² ............................................. C07C 7/13
[58] Field of Search ............ 260/674 SA; 208/310 Z

[56] References Cited

UNITED STATES PATENTS

| | | | |
|---|---|---|---|
| 3,558,730 | 1/1971 | Neuzil | 260/674 |
| 3,878,127 | 4/1975 | Rosback | 260/674 |
| 3,878,129 | 4/1975 | Rosback | 260/674 |
| 3,894,109 | 7/1975 | Rosback | 260/674 |

*Primary Examiner*—Delbert E. Gantz
*Assistant Examiner*—C. E. Spresser
*Attorney, Agent, or Firm*—James R. Hoatson, Jr.; Thomas K. McBride; William H. Page, II

[57] ABSTRACT

A process for the separation of the para-isomer from a hydrocarbon feed mixture comprising at least two bi-alkyl substituted monocyclic aromatic isomers, including the para-isomer, said isomers having from 8 to about 18 carbon atoms per molecule using a specially prepared adsorbent comprising a Y zeolite containing at the exchangeable cationic sites one or more selected cations. The feed mixture is passed through a bed of the adsorbent wherein the para-isomer is preferentially adsorbed within the adsorbent and thereafter recovered from the adsorbent. Novel feature of the process is the use of the specially prepared adsorbents which have faster adsorption-desorption rates for the desired para-isomer.

19 Claims, No Drawings

AROMATIC HYDROCARBON ISOMER SEPARATION PROCESS

CROSS-REFERENCE TO RELATED APPLICATIONS

This application is a continuation-in-part of my prior, copending application Ser. No. 443,043 which was filed on Feb. 15, 1974, now U.S. Pat. No. 3,894,109, all of the teachings of which are incorporated herein by specific reference thereto.

BACKGROUND OF THE INVENTION

1. Field of the Invention

The field of art to which the claimed invention pertains is hydrocarbon separation. More specifically, the invention relates to a process for separating a para-isomer from a feed mixture comprising at least two-bi-alkyl substituted monocyclic aromatic isomers, including the para-isomer, the isomers having from 8 to about 18 carbon atoms per molecule which process employs specially prepared zeolitic adsorbent which selectively removes the para-isomer from the feed.

2. Description of the Prior Art

I have discovered that ion-exchange particles of a base material comprising type X or type Y zeolite and amorphous material as a binder with an aqueous solution of sodium hydroxide prior to the ion exchange with certain selected cations produces an adsorbent possessing faster adsorption-desorption rates when used to separate the para-isomer from a feed mixture comprising at least two bi-alkyl substituted monocyclic aromatic isomers, including the para-isomer, the isomers having from 8 to about 18 carbon atoms per molecule. The reason for this is not entirely understood but it is hypothesized that the ion-exchange of the base material with aqueous sodium hydroxide replaces extraneous non-sodium cations, such as H+ or Group IIA cations, present in the base material and occupying exchangeable sites within the zeolite thereby permitting higher amounts of the selected cations to be added during a subsequent ion-exchange step.

It is known in the separation art that certain adsorbents comprising crystalline aluminosilicates and containing selected cations can be used in processes to separate hydrocarbon isomers from feed mixtures containing such isomers. For example, U.S. Pat. Nos. 3,558,730; 3,558,732; 3,626,020; 3,663,638; and 3,734,974 teach the use of adsorbents comprising X or Y zeolites and selected cations in a process for the separating a specific para-isomer, para-xylene, from a mixture of $C_8$ aromatic hydrocarbons.

The prior art has also recognized that the certain properties or characteristics of various zeolites can be modified by treating the zeolites with various substances. Typically, zeolites are treated to eliminate or suppress an undesireable characteristic such as acidity which may bring about such acid-catalyzed reactions as isomerization and polymerization. Various zeolites may also be treated to enhance a particularly desired characteristic when employed in specific processes.

U.S. Pat. 3,382,039 for example relates to a process for increasing the exchange capacity of silver zeolites over that of known silver zeolites and their use in providing potable water from saline waters. U.S. Pat. No. 3,326,797, for example, discloses a process for aqueous caustic treating of high silica zeolites having silica over alumina ratios between about 6 and 12, at treating conditions, for the sole purpose of removing a certain percentage of structural silica from the zeolite. The caustic treatment, at conditions to preferably retain a final $SiO_2Al_2O_3$ ratio greater than about 5.5, is found to increase the adsorptive capacity of the zeolite and to increase its catalytic activity when used in hydrocatalytic conversion processes such as olefin hydrogenation, hydrocracking, and desulfurization. The caustic treating process of that reference patent is concerned only with etching or leaching of silica from the zeolite structure to achieve these characteristics.

The prior art references either alone or in combination, however, do not disclose or suggest the adsorbent preparation method of this invention or the aromatic isomer separation process of this invention which process employs the adsorbent so produced.

SUMMARY OF THE INVENTION

It is, accordingly, one broad object of my invention to provide a method for preparing an adsorbent comprising a zeolite containing selected cations at the exchangeable cationic sites which adsorbent possesses improved properties when employed in an aromatic hydrocarbon isomer separation process. It is also a broad object of my invention to provide a process which employs the adsorbent produced by the method of my invention to effect the separation of para-isomer from a feed mixture comprising at least two-bi-alkyl substituted aromatic isomers, including the para-isomer, the isomers having from 8 to about 18 carbon atoms per molecule. More specifically, it is an objective of my invention to provide a process which employs the specially prepared adsorbent to effect the separation of para-xylene from a feed mixture comprising para-xylene and at least one other $C_8$ aromatic isomer.

In brief summary, my invention is, in one embodiment, a process for separating the para-isomer from a feed mixture comprising at least two bi-alkyl substituted monocyclic aromatic isomers, including the para-isomer, said isomers having from 8 to about 18 carbon atoms per molecule which process comprises contacting said mixture with an adsorbent prepared by the steps of: (a) contacting a base material comprising Y zeolite with an aqueous sodium hydroxide solution at first ion exchange conditions to effect the addition of sodium cations to said base material; (b) treating the sodium-exchanged base material at second ion exchange conditions to effect the essentially complete exchange of sodium cations with one or more cations selected from the group consisting of potassium, cesium, and rubidium; and, (c) drying the material at conditions to reduce the LOI at 900° C. to less than about 10 wt. % thereby selectively adsorbing at adsorption conditions said para-isomer and thereafter recovering said para-isomer.

Other embodiments and objects of the present invention encompass details about feed mixtures, adsorbents, desorbent materials, and operating conditions all of which are hereinafter disclosed in the following discussion of each of these facets of the present invention.

DESCRIPTION OF THE INVENTION

The type X and type Y crystalline aluminosilicates or zeolites herein contemplated are described as a three-dimensional network of fundamental structural units consisting of silicon-centered $SiO_4$ and aluminum-centered $AlO_4$ tetrahedra interconnected by a mutual sharing of apical oxygen atoms. The space between the tetrahedra is occupied by water molecules and subsequent dehydration or partial dehydration results in a crystal structure interlaced with channels of molecular dimension.

Thus, the crystalline aluminosilicates are often referred to as molecular sieves and separations performed with molecular sieves are generally thought to take place by a physical "sieving" of smaller from larger molecules appearing in the feed mixture. In the separation of aromatic hydrocarbon isomers, however, the separation of the isomers apparently occurs because of differences in electrochemical attraction of the different isomers and the adsorbent rather than on pure physical size differences in the isomer molecules.

In hydrated form, the preferred crystalline aluminosilicates generally encompass those zeolites represented by the formula 1 below:

Formula 1

$$M_{2/n}O:Al_2O_3:wSiO_2:yH_2O$$

where M is a cation which balances the electrovalence of the tetrahedra and is generally referred to as an exchangeable cationic site, $n$ represents the valence of the cation, $w$ represents the moles of $SiO_2$, and $y$ represents the moles of water. The cations may be any one of a number of cations which will hereinafter be described in detail.

Adsorbents comprising the type X structured and type Y structured zeolites are especially preferred for the adsorptive separation of aromatic hydrocarbon isomers. These zeolites are described and defined in U.S. Pat. Nos. 2,882,244 and 3,120,007 respectively. The terms "type X structured" and "type Y structured" zeolites as used herein shall include all zeolites which have general structures as represented in the above two cited patents.

The type X structured zeolite in the hydrated or partially hydrated form can be represented in terms of mole oxides as shown in formula 2 below:

Formula 2

$$(0.9 \pm 0.2)M_{2/n}O:Al_2O_3:(2.5\pm0.5)SiO_2:yH_2O$$

where M represents at least one cation having a valence of not more than 3, $n$ represents the valence of M, and $y$ is a value up to about 9 depending upon the identity of M and the degree of hydration of the crystal. The cation M may be one or more of a number of cations such as the hydrogen cation, the alkali metal cation, or the alkaline earth cations or other selected cations, and is generally referred to as an exchangeable cationic site.

The type Y structured zeolite in the hydrated or partially hydrated form can be similarly represented in terms of mole oxides as in formula 3 below:

Formula 3

$$(0.9\pm0.2)M_{2/n}O:Al_2O_3:wSiO_2:yH_2O$$

where M is at least one cation having a valence not more than 3, $n$ represents the valence of M, $w$ is a value greater than about 3 up to 8, and $y$ is a value up to about 9 depending upon the identiy of M and the degree of hydration of the crystal.

The term "type X zeolite" and "type Y zeolite" as employed herein shall refer not only to type X structured and type Y structured zeolites containing sodium cations as the cation M indicated in the formulas above but also shall refer to those containing other additional cations such as hydrogen cations, the alkali metal cations, or the alkaline earth cations. Typically both the type X and type Y structured zeolites as initially prepared and as used as a base material for the special adsorbent described herein are predominantly in the sodium form but they usually contain any or all of the cations mentioned above as impurities. The term "exchanged cationic site" generally refers to the site in the zeolite occupied by the cation M. This cation, usually sodium, can be replaced or exchanged with other specific cations, depending on the type of the zeolite to modify characteristics of the zeolite.

The term "base material" as used herein shall refer to a type X or type Y zeolite-containing starting material used to make the special adsorbent described below. Generally the base material will be in the form of particles such as extrudates, aggregates, tablets, pills, macrospheres, or granules produced by grinding any of the above to a desired size range. The type X or type Y zeolite can be present in the base material in concentrations generally ranging from about 75 wt. % to about 98 wt % of the base material based on a volatile free composition. The remaining material in the base material generally comprises amorphous silica or alumina or both which is present in intimate mixture with the zeolite material. This amorphous material may be an adjunct of the manufacturing process of the type X or type Y zeolite (for example, intentionally incomplete purification of the zeolite during its manufacture) or it may be added to the relatively pure zeolite to aid in forming or agglomerating particles of the zeolite.

One example of a base material is commercially available nominal one-sixteenth inch extrudate comprising 13X zeolite and a minor amount of amorphous material as binder. This base material is primarily in the sodium form; that is, the cation represented as M in formula 2 above is primarily sodium. By chemical analysis the $Na_2O/Al_2O_3$ ratio of this base material is usually about 0.7 or less and can typically be about 0.6. This, of course, is less than the 0.9±0.2 indicated in formula 2 above. Other cations such as H+ and any of the Group IIA metal cations may be present, primarily as impurities, to supply the remainder of the cations needed for chemical balance and to meet the 0.9±0.2 $Na_2O/Al_2O_3$ ratio. The silica to alumina ratio of this starting material by X-ray determination is about 2.5 and the same ratio by chemical analysis is about 2.6. Normally the base material, whether in the extrudate or pellet form, is granulated to a particle size range of about 20–40 mesh (Standard U.S. Mesh) before the first ion exchange step is begun. This is approximately the desired particle size of the finished adsorbent.

I have found that treating a type X or type Y base material with a dilute aqueous sodium hydroxide solution prior to a subsequent ion exchange of the treated base material to effect the replacement of sodium cations at the exchangeable cationic sites with one or more other selected cations produces a superior adsorbent when used in a process for the separation of the para-isomer from a hydrocarbon feed mixture comprising at least two bi-alkyl substituted aromatic isomers including the para-isomer, the isomers having from 8 to about 18 carbon atoms per molecule. This treatment step is in the nature of an ion exchange step (and will hereinafter be referred to as the first ion exchange) since the NaOH solution replaces non-sodium impurities in the type X or type Y zeolite contained in the base material thereby converting the zeolite essentially completely to the sodium form. More specifically, to produce an acceptable adsorbent it is preferred that the sodium content of the starting material, as characterized by the weight ratio $Na_2O/Al_2O_3$ be increased to a ratio greater than about 0.70 and more preferably from about 0.75 to 1.0. First ion exchange conditions should be so regulated to achieve this degree of ion exchange.

Increasing the sodium content of the base material appears to permit a higher loading into the zeolite of one or more other selected cations during a second subsequent ion exchange thus producing, for reasons not fully understood, a superior adsorbent. It is these selected cations and the $SiO_2/Al_2O_3$ ratio of the zeolite which determines the adsorbent properties (hereinafter discussed in more detail) which make possible various adsorptive separation processes.

Although mild ion-exchange conditions are employed for this first ion exchange, this step additionally removes a small amount of silica and alumina. Total silica and alumina removal from the base material is from about 1 to about 15% and is generally in the range of about 1 to 5 wt %. Analyses indicate that the bulk of both soluble and insoluble material removed from the base material is aluminum as alumina or sodium aluminate. At least a portion of the alumina extracted appears to be from the zeolite itself rather than from any amorphous material since there is some nominal loss of zeolite as detected by X-ray analysis after this step. It is not known whether the small amount of silica removed from the base material came from the crystalline (zeolite) portion or the amorphous portion of the base material.

The degree of ion exchange and extraction of alumina achieved is a function of the three variables of caustic concentration, temperature at which the ion exchange is conducted, and the length of time the ion exchange is continued.

The sodium hydroxide used to prepare the aqueous sodium hydroxide solution should be of high purity having very low levels of both other Group IA impurities and Group impurities. Suitable concentrations to obtain the desired ion exchange can be from about 0.5 to 10 wt. % of the sodium hydroxide with the preferred concentration being from about 0.5 to 5 wt. %. By using solutions containing sodium hydroxide within these ranges of concentration, the desired ion exchange can be obtained at temperatures from about 50° to 250° F. with temperatures from about 150° to 250° F. being especially preferred. Operating pressure is not critical and need only be sufficient to insure a liquid phase. Operating pressures can range from about atmospheric pressure to about 100 psig. The length of time required for the ion exchange will vary, depending upon the solution concentration and temperature, from about 0.5 to 5 hours. Within the above preferred concentrations and temperature ranges, a contact time which has been shown to be especially preferred is about 2 to 3 hours. Continuous or batch-type operations can be employed. The ion exchange step should be controlled so that the zeolite structure will not be destroyed and so that the final product will have a $Na_2O/Al_2O_3$ ratio greater than about 0.7 and more preferably from about 0.75 to 1.0.

After the first ion-exchange step, the sodium exchanged particles are treated at second ion-exchange conditions to effect the essentially complete exchange of the sodium cations at the exchangeable cationic sites in the zeolite with one or more other selected cations.

The cations which may be placed upon the zeolite include cations selected from, but not limited to, the Group IA, Group IIA, and Group IB metals of the Periodic Table of Elements. More specifically, adsorbents comprising type X or type Y zeolites containing single cations selected from the group consisting of lithium, sodium, potassium, rubidium, cesium, beryllium, magnesium, calcium, strontium, barium, silver, manganese, cadmium, and copper at the exchangeable cationic sites show preferential selectivity for the para-isomer with respect to other bi-alkyl substituted monocyclic isomers. Especially preferred adsorbents containing primarily single cations at the exchangeable cationic sites are an adsorbent comprising type X zeolite containing barium cations at these sites and an adsorbent comprising type Y zeolite containing a cation selected from the group consisting of potassium, cesium, and rubidium at these sites.

Type X or type Y zeolites containing the following combinations of cations have also been shown to be suitable for para-isomer separation. These cations include potassium and barium, potassium and beryllium, potassium and manganese, rubidium and barium, cesium and barium, copper and cadmium, copper and silver, zinc and silver, and copper and potassium, with the barium and potassium combination being preferred. A particularly preferred adsorbent is one comprising type X or type Y zeolite containing barium and potassium at the exchangeable cationic site, in a weight ratio of barium to potassium of from about 1.5 to about 200.

Cationic or base exchange methods are generally known to those familiar with the field of crystalline aluminosilicate production. They are generally performed by contacting the zeolite with an aqueous solution of the soluble salts of the cation or cations desired to be placed upon the zeolite. The desired degree of exchange takes place and then the sieves are removed from the aqueous solution, washed and dried to a desired water content. It is contemplated that cation exchange operations may take place using individual solutions of desired cations to be placed on the zeolite or using an exchange solution containing a mixture of cations, where two or more desired cations are to be placed on the zeolite.

When singular cations are based exchanged upon a zeolite the singular cations can comprise anywhere from 5 up to 75 wt. % on a relative volatile free basis of the zeolite depending upon the molecular weight of the material exchanged upon the zeolite. It is contemplated that when single ions are placed upon the zeolite that they may be on the zeolite in concentrations of from about 1% to about 100% of the original cations present (generally sodium) upon the zeolite prior to its being ion-exchanged. By knowing the empirical formula of the zeolite used, its water content and the percentage of any amorphous material or binder present, if any, it is possible to calculate the percentage of ion exchange that has taken place.

When two or more cations are placed upon the zeolite there is an additional parameter in which one can operate in order to effectively produce a zeolite having the desired properties. Besides the extent of the zeolite ion exchange, which is determined by variables such as the length of ion-exchange times, ion-exchange temperature, and cation concentrations, one can also vary the ratio of individual cations placed on the zeolite. In instances in which the cation pairs comprise a Group IIA metal and a Group IA metal the weight ratio of these two components upon the zeolite can vary anywhere from about less than about one up to about two hundred depending upon the molecular weight of the Group IIA or Group IA metal.

Second ion-exchange conditions will include a temperature of from about 50° to about 250° F. and a pH sufficient to preclude the formation of the hydrogen form of the zeolite. The pH will therefore be greater than 7 and preferably within the range of 7 to 10. Operating pressure is not critical and need only be sufficient to insure a liquid phase. Operating pressures can range from about atmospheric pressure to about 150 psig. The length of time for the essentially complete exchange of the sodium cations will be from about 0.5 to about 5 hours depending upon the concentration of the cation in the ion exchange medium and the temperature. The term "essentially complete exchange" as used herein shall mean that the sodium cation content of the base material has been reduced to about 2.0 wt. % or less and more preferably to about 1 wt. % or less.

When the adsorbent is to contain more than one cation at the exchangeable cationic sites it is preferred that the second ion exchange be done in more than one step, each step being an ion exchange with an aqueous solution containing a single cation. For example, when the adsorbent is to contain both barium and potassium, the sodium exchanged particles, produced by the first ion exchange, may be ion exchanged first with an aqueous solution of a potassium salt, preferably an aqueous solution of potassium chloride, for a time sufficient to reduce the sodium cations to less than about 2 wt. % of the zeolite and yield the potassium form of the zeolite. The exchange can be either a continuous or a batch type operation. The ion-exchange is suitably accomplished on passing a 7 wt. % aqueous potassium chloride solution through a bed of the sodium-exchanged particles at about 180°F. at a liquid hourly space velocity of about one until a total of approximately 13 pounds of solution per pound of said particles has been passed in contact therewith. Small amounts of potassium hydroxide will be added to the ion exchange solution to maintain the pH of the solution within the range of from 7 to about 10. Since the primary purpose of the sodium cation ion exchange was to remove hydrogen cation (and metal cation) contaminants, this pH range is necessary to avoid redepositing hydrogen cation on the adsorbent mass.

The potassium-exchange particles can then be washed with water to remove excess ion-exchange solution. The washing medium will be water to which has been added small amounts of potassium hydroxide to adjust and maintain the pH within the range of 7 to about 10. Washing temperatures can include temperatures within the range of about 100° F. to about 200° F. with a temperature of about 100° to 145° F. preferred. Although the washing step can be done in a batch manner with one aliquot of wash water at a time, the washing step is generally and preferably done on a continuous flow type basis with water passed through a bed of the adsorbent at a given liquid hourly space velocity and a temperature for a period of time in order that from about 1 to about 5 gallons of water per pound of starting material is used to wash the material. Preferred washing conditions include using liquid hourly space velocities from about 0.5 to 5, with 1.5 being preferred, to pass from about 1 to about 3 gallons of wash water per pound of starting materaal over the ion exchanged adsorbent.

The potassium-exchanged particles will then be ion exchanged with an aqueous solution of a barium salt in the second step of the two-step ion-exchange procedure to achieve the desired weight ratio of barium to potassium on the finished adsorbent. Preferably an aqueous solution of from about 0.2 to about 5 wt. % barium chloride is recycled through the particle bed at about 180° F. and at a liquid hourly space velocity of from about 1 to about 5 until the desired degree of exchange has been achieved. After the barium-exchange step is completed, the water-washing step is repeated, again maintaining a pH of 7 or greater in order to prevent the possibility of formation of the hydrogen form of the zeolite. A good indication of complete washing can be made by quantitatively testing the effluent wash water for the presence of the anion portion of the salt used in the ion exchange solution.

The order of the potassium and barium exchanges could also be reversed with the barium exchange first and the potassium exchange second. This two-step exchange procedure of potassium and barium cations is not necessarily limiting as it has been found possible to employ a single step ion-exchange in which both barium and potassium are placed on the zeolite. The two-step procedure, however, allows more precise control of the amount of cations placed on the zeolite. Although this second ion exchange, whether conducted in one step or two, has been described in terms of potassium and barium it shall, of course, equally apply with other pairs of cations previously described.

When it is desired that the sodium exchanged particles resulting from the first ion exchange be essentially completely exchanged with a single cation, such as barium or potassium, then a procedure like that of the first step alone or the second step alone of the above described two-step procedure will be employed.

When the wash step is completed, the wet adsorbent particles will usually contain from about 30 to about 50 wt. % volatile matter (water) as measured by loss on ignition to 900° C. In this specification, the volatile matter content of the zeolite adsorbent is determined by the weight difference obtained before and after drying a sample of adsorbent in a high temperature furnace at 900° C. under an inert purge gas stream such as nitrogen for a period of time sufficient to achieve a constant weight. The difference in weight, calculated as a percentage of the sample's initial weight, is reported as loss on ignition (LOI) at 900° C. and represents the volatile matter present within the adsorbent.

The remaining step in the method of manufacture then is the drying step to reduce the LOI at 900° C. to less than about 10 wt. % with the preferred LOI being about 3 to 7 wt. %. After the washing has been completed, the particles can be unloaded and dried in a forced air oven at temperatures above the boiling point of water but less than about 500° and preferably about 150° C., for a period of time sufficient to remove enough water so that the volatile matter content of the zeolite is below about 10 wt. %. Other methods of drying may be used which can include drying in the presence of an inert gas or under a vacuum, or both.

Feed stocks which can be used in the adsorption separation process of this invention which employs the adsorbent prepared by the method of this invention are characterized by the formula shown in formula 3 below:

Formula 3

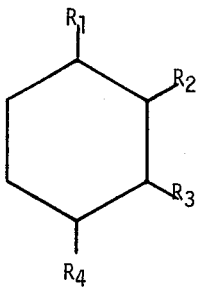

wherein $R_1$, $R_2$, $R_3$, and $R_4$ are selected from the group of alkyl chains in a manner to allow an essentially bi-alkyl substitution at either ortho-, meta-, or para-isomer positions. The R substitutional groups can include alkyl groups ranging from methyl substitution groups up to and including chains having 11 or less carbon atoms per molecule. The alkyl side chains can be both normal and branched in nature and are preferably saturated chains.

Specific representative compounds which can be utilized as feedstocks in the process include those feedstocks containing the xylene isomers and ethylbenzene and the various isomers of methylethylbenzene, diethylbenzene, isopropyltoluene (cymene), the methylpropylbenzenes, ethylpropylbenzenes, methylbutylbenzenes, ethylbutylbenzene, dipropylbenzenes, methylpentylbenzene, etc., and combinations thereof. The above list only represents a small fraction of compounds whose isomers can be separated by the adsorptive-separation process of this invention which employs the specially prepared adsorbent produced by the method of this invention. Thus the process of this invention will be typically used to separate para-xylene from a feed mixture comprising para-xylene and at least one other $C_8$ aromatic isomer; para-diethylbenzene from a feed mixture comprising para-diethylbenzene and at least one other diethylbenzene isomer; and para-cymene from a feed mixture comprising para-cymene and at least one other cymene isomer to name a few.

The isomers of such compounds are separated by this adsorbent according to their configuration depending whether they are of a para-, meta-, or ortho-isomer construction. Specifically, the para-isomer is selectively adsorbed relative to the other isomers. It is contemplated that with feedstocks containing mixtures of more than one class of isomers (for example, $C_8$ isomers in mixture with $C_9$ or $C_{10}$ isomers) molecular weight differences will unduly interfere with selective adsorption based upon isomer configuration differences. It is therefore preferred that the process utilizing the adsorbent produced by the method of this invention to employ feedstocks comprising only a single class of aromatic isomers, that is, aromatic isomers having an equal number of carbon atoms per molecule. It is more preferable to use isomers having as their only differences the location of the alkyl substituted groups in a para-, meta-, or ortho-position. The alkyl structures should preferably be the same for each isomer of a class. In some instances an isomer may have alkyl chains which are both normal or branched or one branched and one normal.

The feedstocks may contain small quantities of straight or branched chain paraffins, cycloparaffins, or olefinic material. It is preferable to have these quantities at a minimum amount in order to prevent contamination of products from this process by materials which are not selectively adsorbed or separated by the adsorbent. Preferably the above-mentioned contaminants should be less than about 20% of the volume feedstock passed into the process.

To separate the para-isomer from a feed mixture containing para-isomer and at least one other aromatic isomer the mixture is contacted with an adsorbent comprising a crystalline aluminosilicate and the para-isomer is more selectively adsorbed and retained by the adsorbent while the other isomers are relatively unadsorbed and are removed from the interstitial void spaces between the particles of adsorbent and the surface of the adsorbent. The adsorbent containing the more selectively adsorbed para-isomer is referred as a "rich" adsorbent--rich in the more selectively adsorbed para-isomer.

The more selectively adsorbed feed component is commonly referred to as the extract component of the feed mixture, while the less selectively adsorbed component is referred to as the raffinate component. Fluid streams leaving the adsorbent comprising an extract component and comprising a raffinate component are referred to, respectively, as the extract stream and the raffinate stream. Thus, the raffinate stream will contain as raffinate components all of the feed mixture isomers except the para-isomer and the extract stream will contain the para-isomer as the extract component.

Although it is possible by the process of this invention to produce high purity (98% or greater), para-isomer product at high recoveries, it will be appreciated that an extract component is never completely adsorbed by the adsorbent, nor is a raffinate component completely non-adsorbed by the adsorbent. Therefore, small amounts of a raffinate compoennt can appear in the extract stream, and, likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed para-isomer to the concentration of less selectively adsorbed meta-isomer will be highest in the extract stream, next highest in the feed mixture, and lowest in the raffinate stream. Likewise, the ratio of the less selectively adsorbed meta-isomer to the more selectively adsorbed para-isomer will be highest in the raffinate stream, next highest in the feed mixture, and the lowest in the extract stream.

The adsorbent can be contained in one or more chambers where through programmed flow into and out of the chambers separation of para-isomer is effected. The adsorbent will preferably be contacted with a desorbent material which is capable of displacing the adsorbed para-isomer from the adsorbent. An extract stream comprising the para-isomer and desorbent material separated thereby leaving high purity para-isomer. Alternatively, the para-isomer could be removed from the adsorbent by purging or by increasing the temperature of the adsorbent or by decreasing the pressure of the chamber or vessel containing the adsorbent or by a combination of these means.

The adsorbent may be employed in the form of a dense compact fixed bed which is alternatively contacted with the feed mixture and a desorbent material (hereinafter described in more detail). In the simplest embodiment of the invention the adsorbent is employed in the form of a single static bed in which case the process is only semi-continuous. A set of two or more static beds may be employed in fixed-bed contacting with appropriate valving so that the feed mixture is passed through one or more adsorbent beds while the desorbent material is passed through one or more of the other beds in the set. The flow of feed mixture and desorbent material may be either up or down through the desorbent. Any of the conventional apparatus employed in static bed fluid-solid contacting may be used. Countercurrent moving-bed or simulated countercurrent moving-bed liquid flow systems, however, have a much greater separation efficiency than fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred processing flow scheme which can be utilized to effect the process of this invention includes what is known in the art as the simulated moving-bed countercurrent system. The general operating sequence of such a flow system is described in U.S. Pat. No. 2,985,589 issued to D. B. Broughton, and more specifically in U.S. Pat. Nos. 3,558,730; 3,558,732; 3,626,020; 3,663,638; and 3,686,342. These patents describe the processing sequence of the 2,985,589 patent employed in particular simulated moving-bed countercurrent solid-fluid contacting processes. The processing sequence disclosed in these patents is the preferred mode of operating the separation process disclosed herein.

One embodiment of this process is a process for separating the para-isomer from a feed mixture containing at least two bi-alkyl substituted monocyclic aromatic isomers, including the para-isomer, said isomers having from 8 to about 18 carbon atoms per molecule which process generally employs the operating sequence described in U.S. Pat. No. 2,985,589 and which comprises the steps of: contacting the feed mixture with the specially prepared adsorbent at adsorption conditions to effect the selective adsorption of para-isomer from the adsorbent, withdrawing from the bed of adsorbent a raffinate stream comprising less selectively adsorbed aromatic isomers, contacting the adsorbent with a desorbent material at desorption conditions to effect desorption of para-isomer from the adsorbent, and withdrawing a stream containing the para-isomer and desorbent from the adsorbent.

Adsorption and desorption conditions for adsorptive separation processes can generally be either in the liquid or vapor phase or both but for aromatic isomer separation processes employing zeolitic adsorbents all liquid-phase operations are usually preferred because of the lower temperature requirements and the slightly improved selectivities associated with the lower temperatures. Preferred adsorption conditions for the process of this invention will include temperatures within the range of from about 100° to about 450° F. and will include pressures in the range from about atmospheric to about 500 psig. Pressures higher than about 500 psig. do not appear to affect the selectivity to a measureable amount and additionally would increase the cost of the process. Desorption conditions for the process of the invention shall generally include the same range of temperatures and pressures as described for adsorption operations. The desorption of the selectively adsorbed isomer could also be effected at substmospheric pressures or elevated temperatures or both or by vacuum purging of the adsorbent to remove the adsorbed isomer but this process is not directed to these desorption methods.

The desorbent materials which can be used in the various processing schemes employing this adsorbent will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

However, in adsorptive separation processes which employ zeolitic adsorbents and processes which are generally operated at substantially constant pressures and temperatures to insure liquid phase, the desorbent material relied upon must be judiciously selected to satisfy several criteria. First, the desorbent material must displace the adsorbed feed component from the adsorbent with reasonable mass flow rates without itself being so strongly adsorbed as to unduly prevent the extract component from displacing the desorbent material in a following adsorption cycle. Secondly, desorbent materials must be compatable with the particular adsorbent and the particular feed mixture. More specifically, they must not reduce or destroy the critical selectivity of the adsorbent for the extract component with respect to the raffinate components.

Desorbent materials to be used in the process of this invention should additionally be substances which are easily separable from the feed mixture that is passed into the process. In desorbing the preferentially adsorbed component of the feed, both desorbent material and the extract component are removed in admixture from the adsorbent. Without a method of separation such as distillation of these two materials, the purity of the extract component of the feed stock would not be very high since it would be diluted with desorbent. It is therefore contemplated that any desorbent material used in this process will have a substantially different average boiling point than that of the feed mixture. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture.

Preferred desorbent materials for use in the process of this invention are those comprising toluene and diethylbenzene. Mixture of these compounds with paraffins are also effective as desorbent materials. Such paraffins must be compatable with the adsorbent and feed mixture as described above and must be easily separable from the feed mixture. The paraffins can include straight or branched chain paraffins or cycloparaffins which meet these criteria. Typical concentrations of toluene or diethylbenzene in mixtures of same and a paraffin can be from a few volume percent up to near 100 vol. % of the total desorbent material mixture but such concentrations preferably will be within the range of from about 50 vol. % to about 100 vol. % of the mixture.

The improved adsorbent produced by the method of my invention can be better understood by brief reference to certain adsorbent properties which are necessary to the successful operation of a selective adsorption process. It will be recognized that improvements in any of these adsorbent characteristics will result in an improved separation process. Among such characteristics are: adsorptive capacity for some volume of an extract component per volume of adsorbent; the selective adsorption of an extract component with respect to a raffinate component and the desorbent material; sufficiently fast rates of adsorption and desorption of the extract component to and from the adsorbent; and, in instances where the components of the feed mixture are very reactive, little or no catalytic activity for undesired reactions such as polymerization and isomerization.

Capacity of the adsorbent for adsorbing a specific volume of an extract component is, of course, a necessity; without such capacity the adsorbent is useless for adsorptive separation. Furthermore, the higher the adsorbent's capacity for an extract component, the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristics is the ability of the adsorbent to separate components of the feed; or, in other words, that the adsorbent possess adsorptive selectivity for one component as compared to another component. Some adsorbents demonstrate acceptable capacity but possess little or no selectivity. Relative selectivity can be expressed not only for one feed mixture component as compared to another but can also be expressed between any feed mixture component and the desorbent. The relative selectivity, (B), as used throughout this specification is defined as the ratio of two components of an adsorbed phase over the ratio of the same two components in an unadsorbed phase at equilibrium conditions.

Relative selectivity is shown as Equation 1 below:

EQUATION 1

$$\text{Selectivity} = (B) = \frac{[\text{vol. percent C/vol. percent D}]_A}{[\text{vol. percent C/vol. percent D}]_U}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Desorbent materials ideally would have a selectivity equal to about 1 or slightly less than 1 with respect to an extract component.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

The adsorbent produced by the method of this invention not only has good aromatic capacity and good selectivity but has faster transfer rates than does an adsorbent not produced by this method.

It is also necessary that the adsorbent possess little or no catalytic activity toward any reaction such as polymerization or isomerization of any of the feed components. Such activity might effect adsorbent capacity or selectivity or product yields or all of these, but in the adsorptive separation of aromatic hydrocarbon isomers with a zeolite containing adsorbent this is generally not a problem.

In order to test various adsorbents and desorbent material with a particular feed mixture to measure the adsorbent characteristics of adsorptive capacity and selectivity and exchange rate a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze the effluent stream leaving the adsorbent chamber.

A pulse test, performed using this apparatus and the following general procedure, is used to determine selectivities and other data for various adsorbent systems. The adsorbent was filled to equilibrium with a particular desorbent by passing the desorbent through the adsorbent chamber. At a convenient time, a pulse of feed containing known concentrations of a non-adsorbed paraffinic tracer (n-nonane) and of aromatic isomers all diluted in desorbent is injected for a duration of several minutes. Desorbent flow is resumed, and the tracer and the aromatic isomers are eluted as in a liquid-solid chromatographic operation. The effluent is analyzed by on-stream chromatographic equipment and traces of the envelopes of corresponding component peaks are developed.

From information derived from the chromatographic traces adsorbent performance can be rated in terms of capacity index for the para-isomer, selectivity for the para-isomer with respect to the other isomers and rate of desorption of the para-isomer by the desorbent. The capacity index is characterized by the distance between the center of the para-isomer peak envelope and the $C_9$ tracer peak envelope. It is expressed in terms of the volume in cubic centimeters of desorbent pumped during this time interval. Selectivity, (B), for para-isomer with respect to the other isomers (p/m, p/o) is characterized by the ratio of the distance between the center of the para-isomer peak envelope and the $C_9$ tracer peak envelope to the corresponding distance for the other isomers. The transfer rates are, we have found, best characterized by the width of the $C_9$ tracer peak envelope at half intensity. The narrower the peak width, the faster the desorption rate.

To further evaluate promising adsorbent systems and to translate this type of data into a practical aromatic separation process requires actual testing of the best system in a continuous countercurrent liquid-solid contacting device.

The general operating principles of such a device have been previously described and are found in Broughton U.S. Patent 2,985,589 and a specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on adsorbent testing and evaluation may be found in the paper "Separation of $C_8$ Aromatics by Adsorption" by A. J. deRosset, R. W. Neuzil, A. J. Korous, and D. H. Rosback presented at the American Chemical Society, Los Angeles, Calif., Mar. 28-Apr. 2, 1971.

The superior performance of these specially prepared adsorbents which was indicated by the pulse test results was confirmed by continuous testing in this device.

The examples shown below are intended to further illustrate both the method of this invention and the process of this invention and are not to be construed as unduly limiting the scope and spirit of either. The examples present pulse test results for various adsorbents. Testing of the various adsorbents was done with $C_8$ aromatics because of easy availability and ease of analysis.

EXAMPLE I

In this example a specific crystalline aluminosilicate adsorbent was prepared by the method of this invention.

Nominal one-sixteenth-inch extrudate containing type 13X zeolite was ground to produce 16–40 U.S. Standard Mesh particle size material having chemical and physical properties as shown in Table No. 1 below:

Table No. 1

| Properties of the Starting Material | |
|---|---|
| Chemical Properties | |
| Volatile Matter (loss on ignition at 900° C.), wt. % | 3.2 |
| $SiO_2$ (volatile free) wt. % | 50.7 |
| $Al_2O_3$ (volatile free) wt. % | 33.6 |
| $Na_2O$ (volatile free) wt. % | 12.4 |
| $Na_2O/Al_2O_3$ | .61 |
| $SiO_2/Al_2O_3$ | 2.56 |
| Physical Properties | |
| Apparent Bulk Density, gm/cc | 0.635 |
| Surface Area, m²/gm | 500 |
| Pore Volume, ml/gm | 0.30 |
| Pore Diameter, A | 24 |
| Area % faujasite (X-ray) | 93 |
| $SiO_2/Al_2O_3$ (X-ray) | 2.5 |

One hundred pounds of the granular base material was loaded into an ion exchange tower against an upward flow of 1.6 wt. % NaOH solution at a rate such that the effluent temperature did not exceed 145° F. After all of the material was loaded, the material was ion exchanged by passing the 1.6 wt. % NaOH solution upflow through the ion exchange tower at a liquid hourly space velocity of 1.5 and a temperature of 200° F. until a total of 0.335 pounds of NaOH per pound of volatile-free starting material had been passed through the tower. After this first ion exchange, the material was water-washed to remove excess NaOH solution by passing treated water, having a pH of 9, upflow through the tower at 1.5 LHSV and 140° F. to a total of 1.3 gallons of water per pound of volatile free starting material. Test samples of particles removed after this wash had the properties as shown in Table No. 2.

Table No. 2

| Properties of the Sodium-exchanged Material | |
|---|---|
| Chemical Properties | |
| Volatile Matter (loss on ignition at 900° C.), wt. % | 25.4 |
| $SiO_2$ (volatile free) wt. % | 48.0 |
| $Al_2O_3$ (volatile free) wt. % | 32.1 |
| $Na_2O$ (volatile free) wt. % | 15.8 |
| $Na_2O/Al_2O_3$ | 0.81 |
| $SiO_2/Al_2O_3$ | 2.54 |
| Physical Properties | |
| Apparent Bulk Density, gm/cc | 0.671 |
| Surface Area, m²/gm | 516 |
| Pore Volume, ml/gm | 0.27 |
| Pore Diameter, A | 21 |
| Area % faujasite (X-ray) | 110 |
| $SiO_2/Al_2O_3$ (X-ray) | 2.5 |

The second ion-exchange conditions were then effected to produce a barium-potassium exchanged type X structured zeolite by the two-step procedure previously described. A potassium chloride solution was first passed over the particles at 180° F. and at one liquid hourly space velocity until a total of about 12 pounds of a 6.9 wt. % potassium chloride solution had contacted about one pound of the particles. After the ion-exchange solution had been expended the particles were essentially totally potassium exchanged and were thereafter water washed at a three liquid hourly space velocity in the manner previously described until the effluent water removed from the particles was essentially chloride-free. After the water-washing step had been completed the particles were then ion exchanged with a 2.4 wt. % barium chloride solution at 180° F. The second step of the ion-exchange conditions were continued until test samples of particles removed during this step indicated that the approximate ratio of the weight of barium over potassium present within the zeolite was within the range of from about 1.5 to about 200. After the barium exchange the particles were again water washed at approximately 9 pH until the effluent water was essentially chloride free.

The washed material was then dewatered, unloaded from the ion exchange tower, and dried in a forced air oven at 570° F. to a volatile content of about 2.0 wt. %. Properties of the finished adsorbent are shown in Table No. 3 below:

Table No. 3

| Properties of the Finished Adsorbent | |
|---|---|
| Chemical Properties | |
| Volatile Matter (LOI at 900° C.), wt. % | 2.2 |
| $SiO_2$ (volatile free) wt. % | 42.1 |
| $Al_2O_3$ (volatile free) wt. % | 28.3 |
| $Na_2O$ (volatile free) wt. % | 2.0 |
| $K_2O$ (volatile free) wt. % | 6.1 |
| BaO (volatile free) wt. % | 20.3 |
| $SiO_2/Al_2O_3$ | 2.52 |

EXAMPLE II

In this example, five adsorbents were tested in a dynamic testing apparatus to illustrate desired properties achieved by the method of this invention. Adsorbent A was a sample of the adsorbent prepared in Example I above; adsorbents B and C were adsorbents prepared similar to the procedure set forth in Example I above but with different Ba/K weight ratios than that of adsorbent A; adsorbents D and E were adsorbents prepared from the same base material of Example I but without the sodium ion exchange step that was used in the preparation of adsorbents A, B, and C.

The dynamic testing apparatus and the pulse test have been previously described. The pulse test is a testing method by which certain adsorbent characteristics can be obtained.

The five adsorbents were tested using this test method to determine the selectivity of the adsorbent particles for para-xylene relative to the other $C_8$ aromatic isomers and to determine the rate of desorption of para-xylene by a particular desorbent. The feed mixture used contained 5 vol. % para-xylene, 5 vol. % meta-xylene, 5 vol. % ortho-xylene, 5 vol. % ethylbenzene, 5 vol. % of normal $C_9$ paraffin which was used as a tracer, and 75 vol. % of an inert hydrocarbon material. The desorbent employed was toluene. All of the adsorbents were dried in situ to less than about 3 wt. % volatile matter as measured at 900° C.

The dynamic testing apparatus was maintained at a controlled temperature of 150° C. with sufficient pressure on the entire testing unit to maintain essentially liquid phase operations. By alternate passage of feed stock and desorbent into the testing unit and constant monitoring of the effluent from the chamber with chromatographic equipment, traces of the envelopes of component peaks were developed. From these traces data can be obtained, in the manner previously described, which will characterize various adsorbent properties.

The results of the adsorptive testing for the five adsorbents are shown in Table No. 4 below.

Table No. 4

| Adsorbent Designation | Sodium Ion Exchange | Wt. % BaO | Wt. % $K_2O$ | Testing Results Wt. Ratio Ba/K | Selectivities P/EB | P/M | P/O | Peak Width in cc |
|---|---|---|---|---|---|---|---|---|
| A | YES | 20.3 | 6.1 | 3.6 | 2.23 | 2.70 | 2.13 | 9.7 |
| B | YES | 24.1 | 5.2 | 5.0 | 2.51 | 2.90 | 2.24 | 8.7 |
| C | YES | 30.1 | 0.6 | 54.1 | 2.78 | 3.12 | 2.34 | 9.4 |
| D | NO | 22.0 | 5.9 | 4.0 | 2.20 | 2.89 | 2.34 | 12.2 |
| E | NO | 25.7 | 2.7 | 10.3 | 2.55 | 2.65 | 2.09 | 10.9 |

As can be seen from the above data in Table No. 4, all five adsorbents tested were preferentially selective for adsorbing para-xylene with respect to the other $C_8$ aromatics. As can be seen, however, the adsorbents A, B, and C prepared by the method of this invention exhibit increased para-xylene selectivity with respect to all of the other $C_8$ aromatic isomers as the weight ratio of Ba/K increases. With adsorbents D and E, which were not prepared by this method, para-xylene ethylbenzene selectivity increases with increasing Ba/K but para/meta and para/ortho selectivities do not. For this reason the presence of an additional cation such as potassium had therefore been found essential prior to the method of this invention to provide suitable para/meta and para/ortho selectivity to complement the para/ethylbenzene provided by the presence of the barium cation. by the method of my invention a barium-containing adsorbent having suitable para-xylene selectivities with respect to all other $C_8$ aromatic isomers can be produced without the requirement of an additional cation.

Table No. 4 also shows that the adsorbents produced by the method of this invention have faster rates of para-xylene adsorption-desorption. These relative rates can be characterized by the width of the normal $C_9$ tracer at half intensity; the narrower the peak width, the faster the adsorption-desorption rates. As shown, the tracer peak widths for adsorbents A, B, and C which were prepared by the method of this invention are narrower than those for adsorbents D and E and therefore possess the faster adsorption-desorption rates.

I claim as my invention:

1. A process for separating the para-isomer from a feed mixture comprising at least two bi-alkyl substituted monocyclic aromatic isomers, including the para-isomer, said isomers having from 8 to about 18 carbon atoms per molecule, which process comprises contacting said mixture with an adsorbent prepared by the steps of:
   a. contacting a base material comprising Y zeolite with an aqueous sodium hydroxide solution at first ion exchange conditions to effect the addition of sodium cations to said base material;
   b. treating the sodium-exchanged base material at second ion exchange conditions to effect the essentially complete exchange of sodium cations with one or more cations selected from the group consisting of potassium, cesium, and rubidium; and,
   c. drying the material at conditions to reduce the LOI at 900° C. to less than about 10 weight percent thereby selectively adsorbing at adsorption conditions said para-isomer and thereafter recovering said para-isomer.

2. The process of claim 1 further characterized in that said para-isomer is para-xylene and said feed mixture comprises para-xylene and at least one other $C_8$ aromatic isomer.

3. The process of claim 1 further characterized in that said para-isomer is para-diethylbenzene and said feed mixture comprises paradiethylbenzene and at least one other diethylbenzene isomer.

4. The process of claim 1 further characterized in that said para-isomer is para-cymene and said feed mixture comprises para-cymene and at least one other cymene isomer.

5. The process of claim 1 further characterized in that said cation is potassium.

6. The process of claim 1 further characterized in that said adsorption conditions are selected from a temperature within the range of from about 70° to about 450° F. and a pressure within the range of from about atmospheric to about 500 psig. to maintain liquid phase.

7. The process of claim 1 further characterized in that said base material has a $Na_2O/Al_2O_3$ ratio of less than about 0.7.

8. The process of claim 1 further characterized in that said first ion exchange conditions include a temperature within the range of from about 50° to about 250° F. and a sodium hydroxide solution concentration of from about 0.5 to about 10 weight percent.

9. The process of claim 1 further characterized in that said sodium-exchanged base material has a $Na_2O/Al_2O_3$ ratio greater than 0.7.

10. The process of claim 1 further characterized in that said second ion exchange conditions include a pH sufficient to preclude formation of the hydrogen form of the zeolite, and a temperature within the range of from about 50° to about 250° F.

11. A process for separating the para-isomer from a feed mixture comprising at least two bi-alkyl substituted monocyclic aromatic isomers, including the para-isomer, said isomers having from 8 to about 18 carbon atoms per molecule, which process comprises the steps of:
   a. contacting at adsorption conditions said mixture with an adsorbent prepared by the steps hereinafter enumerated to effect the selective adsorption of para-isomer;
   b. withdrawing from the adsorbent a stream comprising less selectively adsorbed aromatic isomers;
   c. contacting the adsorbent with a desorbent material at desorption conditions to effect desorption of para-isomer from the adsorbent; and,
   d. withdrawing from the adsorbent a stream containing the para-isomer and desorbent material;
   wherein the adsorbent is prepared by the steps of:
   i. contacting a base material comprising a Y zeolite having a $Na_2O/Al_2O_3$ ratio less than about 0.7 with an aqueous sodium hydroxide solution at first ion exchange conditions, including a temperature within the range of from about 50° to about 250° F. and a sodium hydroxide solution concentration of from about 0.5 to about 10 weight percent to increase the sodium cation content to a $Na_2O/Al_2O_3$ ratio of greater than about 0.7;
   ii. treating the sodium-exchanged base material at second ion exchange conditions, including a pH sufficient to preclude the formation of the hydrogen form of the zeolite and a temperature within the range of from about 50° to about 250° F., to effect the essentially complete exchange of sodium cations with one or more cations selected from the group consisting of potassium, cesium, and rubidium; and,
   iii. drying the resulting material at conditions sufficient to reduce the LOI at 900° C. to less than about 10 weight percent.

12. The process of claim 11 further characterized in that said para-isomer is para-xylene and said feed mixture comprises para-xylene and at least one other $C_8$ aromatic isomer.

13. The process of claim 11 further characterized in that said para-isomer is para-diethylbenzene and said feed mixture comprises para-diethylbenzene and at least one other diethylbenzene isomer.

14. The process of claim 11 further characterized in that said para-isomer is para-cymene and said feed mixture comprises para-cymene and at one other cymene isomer.

15. The process of claim 11 further characterized in that said cation is potassium.

16. The process of claim 11 further characterized in that said adsorption and desorption conditions are selected from a temperature within the range of from about 70° to about 450° F. and a pressure within the range of from about atmospheric to about 500 psig. to maintain a liquid phase.

17. The process of claim 11 further characterized in that said desorbent material has an average boiling point substantially different than that of the feed mixture.

18. The process of claim 17 further characterized in that said desorbent material comprises diethylbenzene.

19. The process of claim 17 further characterized in that said desorbent material comprises toluene.

* * * * *